(12) United States Patent
Straeter

(10) Patent No.: US 9,382,509 B2
(45) Date of Patent: Jul. 5, 2016

(54) APPARATUS AND METHOD OF USING AN AGRICULTURAL WASTE DIGESTER AND BIOGAS GENERATION SYSTEM

(76) Inventor: James E. Straeter, Rochester, IN (US)

( * ) Notice: Subject to any disclaimer, the term of this patent is extended or adjusted under 35 U.S.C. 154(b) by 630 days.

(21) Appl. No.: 13/362,204

(22) Filed: Jan. 31, 2012

(65) Prior Publication Data

US 2012/0135492 A1 May 31, 2012

Related U.S. Application Data

(63) Continuation-in-part of application No. 12/759,748, filed on Apr. 14, 2010, now Pat. No. 8,129,158.

(51) Int. Cl.
  *C12M 1/107* (2006.01)
  *C12M 3/04* (2006.01)
  *C12M 1/00* (2006.01)
  *C12M 1/02* (2006.01)

(52) U.S. Cl.
  CPC .............. *C12M 21/04* (2013.01); *C12M 27/10* (2013.01); *C12M 27/20* (2013.01); *C12M 41/22* (2013.01); *Y02E 50/343* (2013.01)

(58) Field of Classification Search
  CPC ...... C12M 21/04; C12M 27/10; C12M 41/22; C12M 27/20; Y02E 50/343
  See application file for complete search history.

(56) References Cited

U.S. PATENT DOCUMENTS

| | | | | |
|---|---|---|---|---|
| 3,700,372 A * | 10/1972 | Lalley | ............................ | 425/159 |
| 4,750,454 A | 6/1988 | Santina et al. | | |
| 4,836,918 A * | 6/1989 | Szikriszt | .................... | B01F 9/06 210/151 |
| 4,921,400 A * | 5/1990 | Niskanen | .................... | 415/169.1 |
| 5,132,090 A * | 7/1992 | Volland | .................... | B01D 1/04 261/87 |
| 6,299,774 B1 | 10/2001 | Ainsworth et al. | | |
| 6,342,378 B1 | 1/2002 | Zhang et al. | | |
| 6,572,772 B2 | 6/2003 | Hoyt | | |
| 7,320,753 B2 | 1/2008 | Roos | | |
| 7,560,026 B2 | 7/2009 | Wilson | | |
| 2007/0158264 A1 | 7/2007 | Zhang | | |
| 2008/0032375 A1* | 2/2008 | Hartmann | .................. | B01F 7/04 435/170 |
| 2008/0160591 A1* | 7/2008 | Willson et al. | ................. | 435/132 |

* cited by examiner

*Primary Examiner* — Gautam Prakash
(74) *Attorney, Agent, or Firm* — Zarley Law Firm, P.L.C.

(57) ABSTRACT

An agricultural waste digester and biogas generation system is disclosed that includes a digester assembly having a cylindrical body, a hollow interior, a center axis and a plurality of wheel segments within the interior of the digester assembly. A gas conduit extends from the interior of the digester assembly to a power generation device. Also included is a water vessel containing water, and each of the plurality of wheel segments have an acruate, contoured surface area which restrict biogas movement within the digester assembly to produce induced agitation of agricultural waste.

22 Claims, 6 Drawing Sheets

APPARATUS AND METHOD OF USING AN AGRICULTURAL WASTE DIGESTER AND BIOGAS GENERATION SYSTEM

CROSS REFERENCE TO RELATED APPLICATION

This application is a continuation-in-part of application Ser. No. 12/759,748 filed on Apr. 14, 2010, now U.S. Pat. No. 8,129,158, issued on Mar. 6, 2012.

BACKGROUND OF THE INVENTION

This invention relates to an apparatus and method of using a simplified and scalable agricultural waste digester and biogas generation system. More specifically, this invention is directed to an agricultural waste digester with an agitation system that utilizes the force of trapped gas produced by the digester to further mechanically agitate the agricultural waste without additional energy added to the system such that the rising gas creates a mechanical force which induces agitation.

The use of anaerobic digestion techniques to obtain energy from agricultural and biological wastes has been known and utilized, at least to a limited extent, for years. However, recently the production of biogas from agricultural waste has gained a growing amount of interest for a number of reasons. Primarily, whereas biogas production from agricultural wastes such as animal manure and vegetation compost may have been of limited importance in terms of energy production and pollution control due to the smaller scale of farming operations in the past, today, as farming operations are becoming more technologically advanced and larger than ever in terms of the number of livestock, production, and waste volume, considerations involving pollution and energy use are becoming more important than ever. Notably, with modern scale concentrated animal feeding operations involving thousands or even tens of thousands of animals, the large production of waste volume has made biogas production not only a more viable option in terms of potential energy production, but also an important consideration in terms of pollution control, as such concentrated animal operations can generate large amounts of waste constituting a major threat to the environment, particularly with respect to water supplies, and air quality. Furthermore, apart from considerations attendant to large scale farming operations, the growing importance of the development and use of alternative, sustainable, and environmentally friendly energy sources in both developed and under-developed cultures has produced a renewed interest in the production of biogas from agricultural waste.

Although a variety of systems and devices have been developed to produce biogas from agricultural wastes such as animal manure or organic waste, the majority of known biogas production methods require large, costly components and employ a complicated system of tanks, valves, and the like. Furthermore, known systems either require the use of an agitator powered by a separate energy source and/or utilize rising bubbles of gas for agitation which flow freely through the organic waste carrying material and causing agitation which either require an additional energy source to operate an agitator or result in unpredictable and/or incomplete agitation. As a result, a need has arisen for a low-cost agricultural waste digester and biogas generation system that overcomes these problems.

Therefore a primary object of this invention is to provide an agricultural waste digester and biogas generation system that is scalable.

It is yet another object of this invention to provide an agricultural waste digester and biogas generation system that is simple and inexpensive to construct, operate, and maintain.

A further object of this invention is to provide an agricultural waste digester and biogas generation system that is versatile and effective in the production of biogas for any type of operation regardless of size and/or complexity, ranging from use in primitive, underdeveloped areas to large scale, modern concentrated animal feeding operations.

It is a further object of this invention to provide an agricultural waste digester and biogas generation system with a digester having an internal structure with no internal dead corners to provide more complete digester content mixing.

It is a further object of this invention to provide an agricultural waste digester and biogas generation system with a buoyant digester having an internal structure of a "reverse water wheel" which traps biogas on one side of the wheel and not the other to cause the digester to rotate in heated water without additional energy added to the system.

It is another object of this invention to provide an agricultural waste digester and biogas generation system which utilizes a power source operating via generated biogas to heat the water of the digester.

It is yet another object of this invention to provide an agricultural waste digester that has an internal structure which provides agitation and transport of organic/agricultural waste without the use of an agitator and additional energy added to the system.

It is still another object of this invention to provide an agricultural waste digester with arcuate, contoured interior segments which prevent biogas from moving freely out of the agricultural waste and trap biogas under these segments to utilize the force of the trapped biogas to rotate the digester and induce the agitation of agricultural waste and further production of biogas.

These and other objects, features or advantages of the present invention will become apparent from the specification and claims.

BRIEF SUMMARY OF THE INVENTION

An agricultural waste digester and biogas generation system includes a digester assembly having a cylindrical body, a hollow interior, a center axis and a plurality of wheel segments within the interior of the digester assembly. A gas conduit extends from the interior of the digester assembly to a power generation device. Also included is a water vessel containing water, and each of the plurality of wheel segments have an acruate, contoured surface area which restrict biogas movement within the digester assembly to produce induced agitation of agricultural waste.

DETAILED DESCRIPTION OF THE PREFERRED EMBODIMENT OF THE INVENTION

Figure 1:
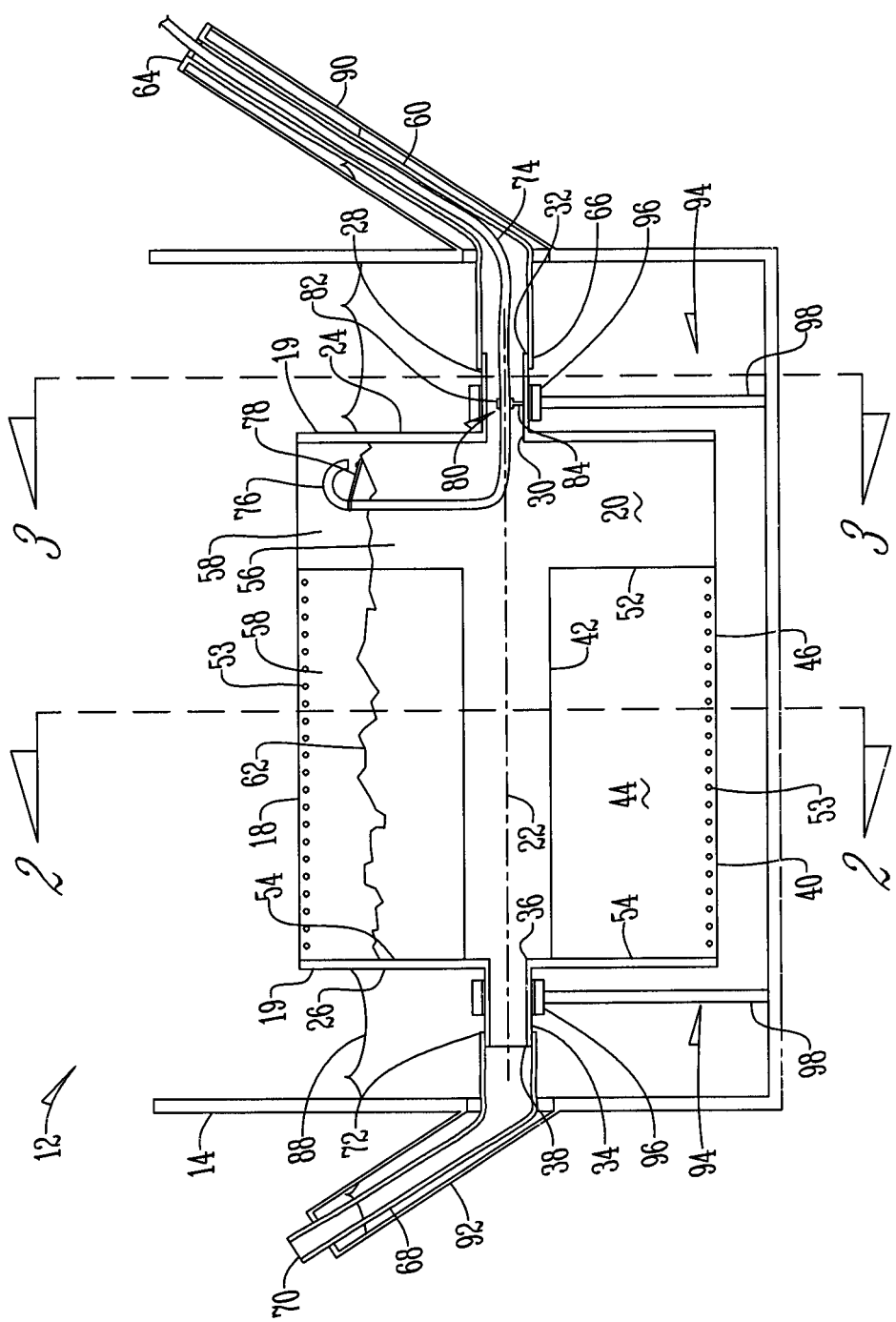
FIG. 1 is a side cross sectional view of the digester assembly of the present biogas production system.
Figure 2:
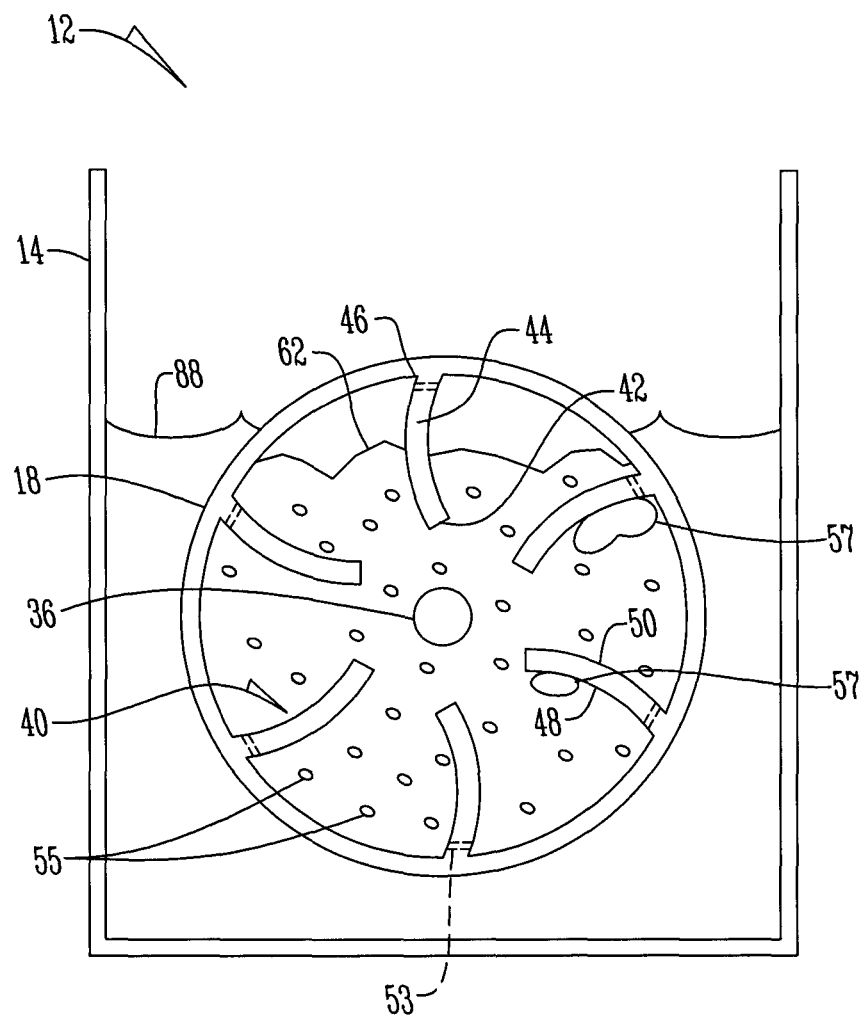
FIG. 2 is a front cross sectional view of the digester assembly of the present biogas production system.
Figure 3:
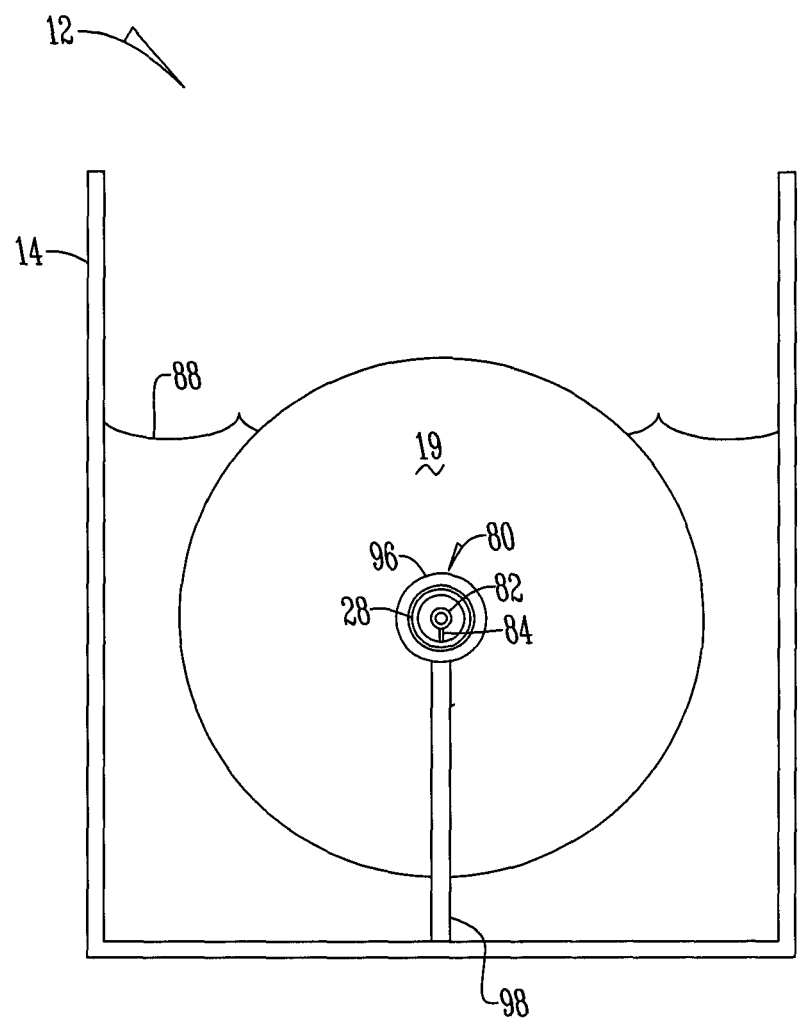
FIG. 3 is a front cross sectional view of the digester assembly of the present biogas production system.
Figure 4:
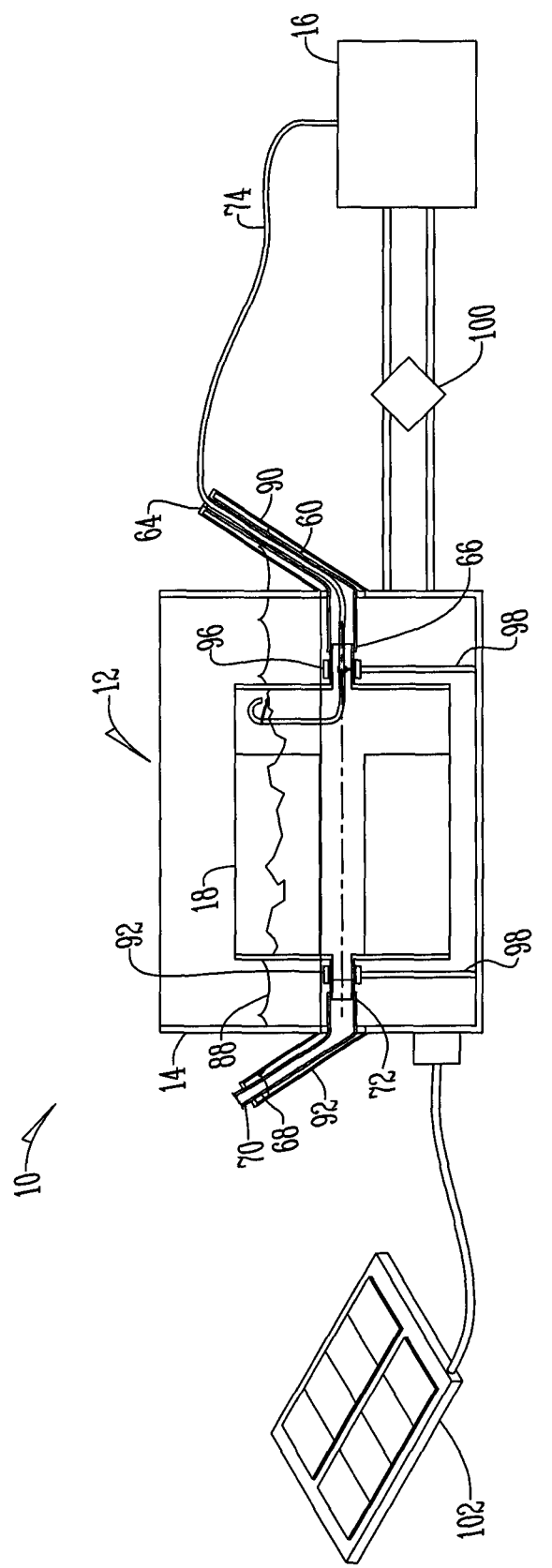
FIG. 4 is a perspective view in partial cross section of the present biogas production system.
Figure 5:
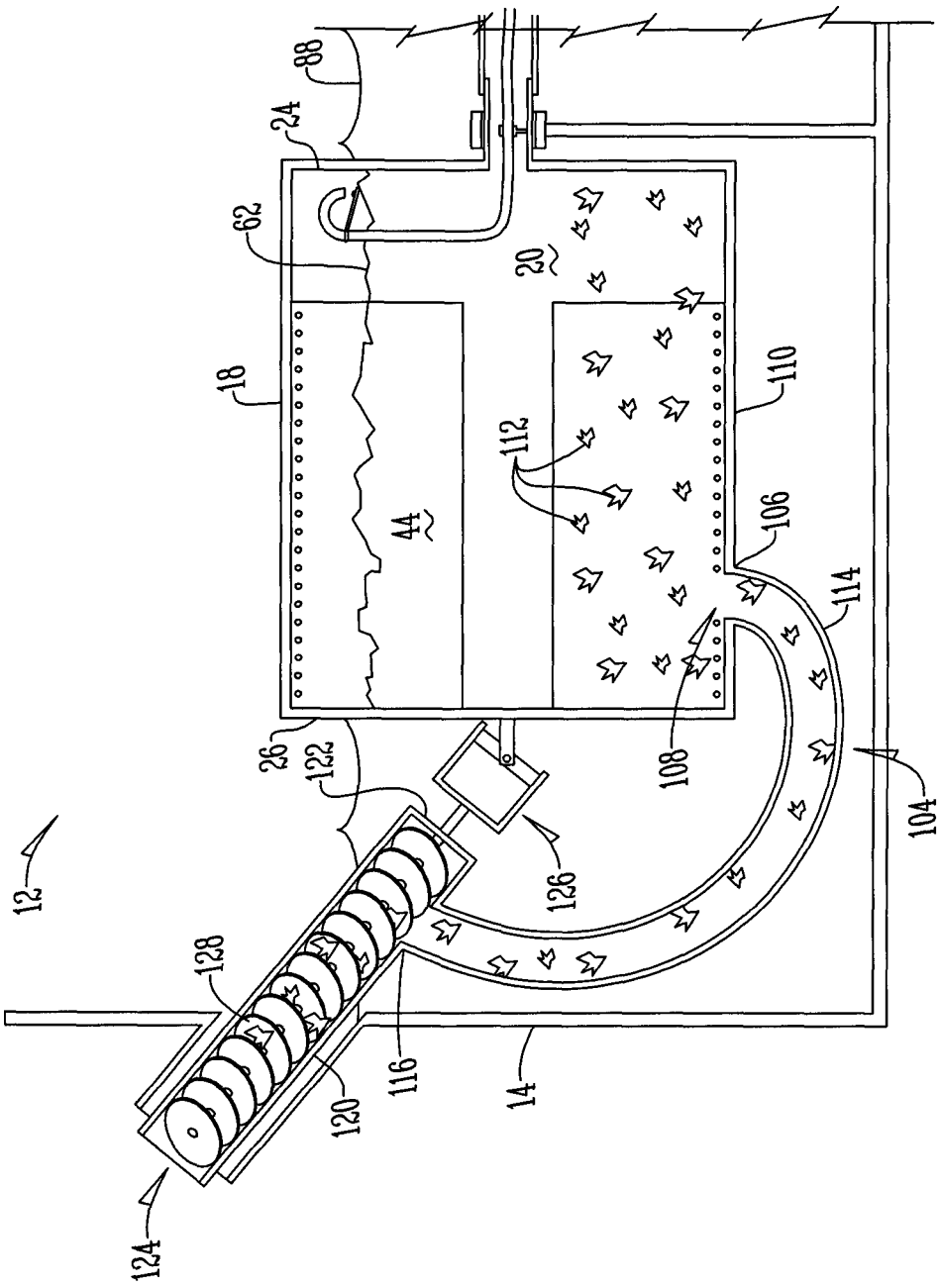
FIG. 5 is a side cross sectional view of an additional embodiment of the digester assembly of the present biogas production system.
Figure 6:
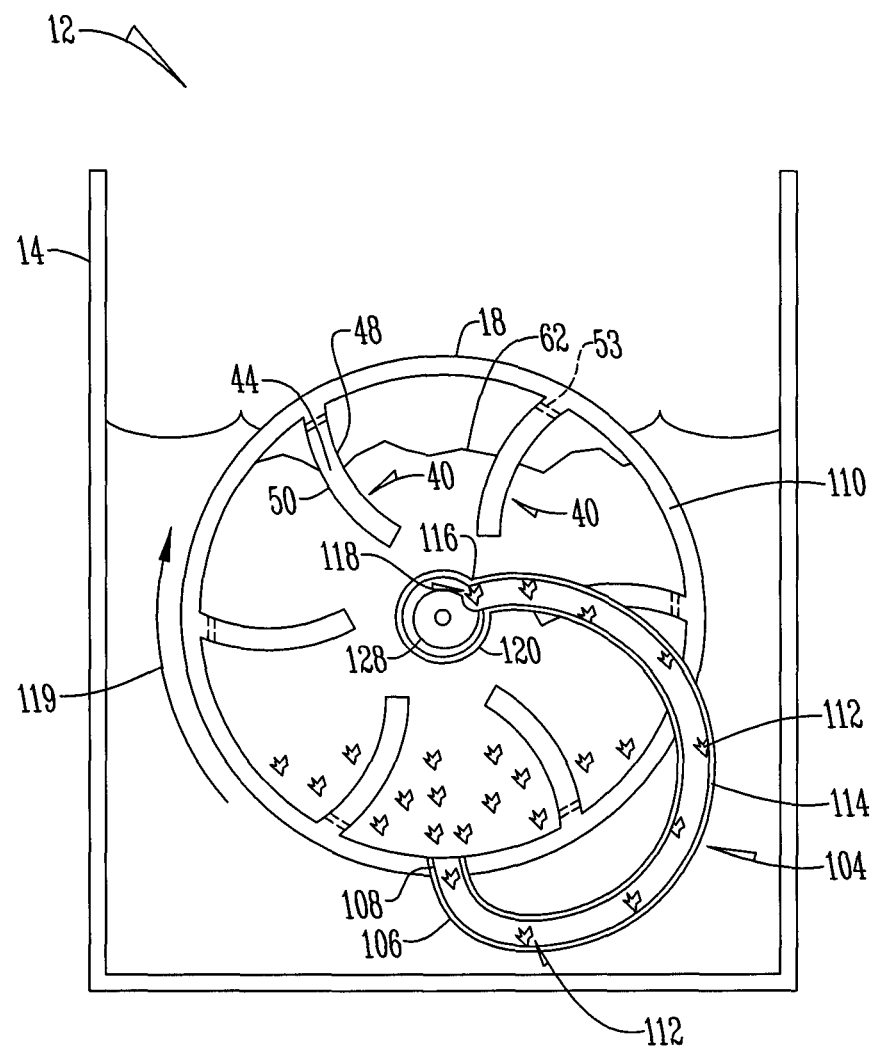
FIG. 6 is a rear cross sectional view of an additional embodiment of the digester assembly of the present biogas production system.

Referring to the figures, an agricultural waste digester and biogas production system 10 includes a digester assembly 12 for anaerobically digesting and generating biogas from agricultural waste 62. In one embodiment, the digested agricultural waste 62 is animal manure and the biogas generated therefrom includes methane and carbon dioxide; alternatively, the agricultural waste 62 is any organic, carbon-based waste capable of producing naturally occurring combustible biogas via an anaerobic digestion process. The agricultural waste digester and biogas production system 10 also includes a water vessel 14 and a power generation device 16.

The digester assembly 12 is composed of any material that permits the digester assembly 12 to float when placed in water while at the same time permits heat to be conducted to the interior of the digester 12 when the digester is partially submerged in heated water to facilitate the process of anaerobic digestion. In one embodiment, the digester assembly 12 is made of a buoyant plastic such as high density polyethylene. Furthermore, the digester assembly 12 is scalable such that the size of the digester assembly 12 can be tailored to suit the particular needs, resources, and applications of the user.

The digester assembly 12 includes a hollow cylindrical body 18 having a hollow interior 20 and a center axis 22. The hollow cylindrical body 18 is enclosed at both ends 19 by a first cover 24 and a second cover 26 affixed to form end walls of the hollow cylindrical body 18. The first cover 24 includes a first hub 28, comprised of a hollow cylindrical segment with open ends aligned with the center axis 22 of the hollow cylindrical body 18 forming an opening in first cover 24 at a first end 30 and having a second end 32 extending outward from the interior 20 of the hollow cylindrical body 18. Similarly, the second cover 26 includes a second hub 34, comprised of a hollow cylindrical segment with open ends aligned with the center axis 22 forming an opening in second cover 26 at a first end 36 and having a second end 38 extending outward from the interior 20 of the hollow cylindrical body 18.

The digester assembly 12 also includes a plurality of wheel segments 40. The plurality of wheel segments 40 are comprised of a series of segments having an arcuate, contoured surface area formed within hollow interior 20 of hollow cylindrical body 18 extending radially from center axis 22 of hollow cylindrical body 18. Each of the plurality of wheel segments 40 includes an inner edge 42 adjacent center axis 22 of hollow cylindrical body 18, an arcuate body 44 having a semicircular, curved surface area extending radially from inner edge 42 to an outer edge 46 fixedly attached to the hollow cylindrical body 18. In one embodiment, each arcuate body 44 is comprised of a concave surface 48 on one side and a convex surface 50 on the other. Furthermore, each arcuate body 44 of each of the plurality of wheel segments 40 is not only uniform in shape to that of each of the other of the plurality of wheel segments 40, but also the contour and orientation of the concave and convex surfaces 48, 50, of each arcuate body 44 is uniformly oriented with respect to each of the other of the plurality of wheel segments 40, with each concave surface 48 of each wheel segment 40 facing a convex surface 50 of an adjacent successive wheel segment 40.

Each of the plurality of wheel segments 40 extends radially within the interior 20 of the hollow cylindrical body 18 from an outer edge 46 fixedly attached to the hollow cylindrical body 18 to an inner edge 42 adjacent center axis 22 extending freely within the hollow interior 20. Each of the plurality of wheel segments 40 extends axially within the interior 20 of the hollow cylindrical body 18 from a second end wall 54 fixedly attached to the second cover 24 to a first end wall 52 extending freely within the hollow interior 20 of the cylindrical body 18 such that an open space or conduit chamber 56 is formed within the cylindrical body's 18 hollow interior 20 between each of the end walls 52 of the plurality of wheel segments 40 and the first cover 24. In one embodiment, each of the plurality of wheel segments 40 includes a plurality of perforations 53 at the outer edge 46 of at each arcuate body 44 adjacent to the attachment point between each wheel segment 40 and the hollow cylindrical body 18. Biogas bubbles 55 accumulate into individual gas pockets 57 under the concave surfaces 48 of each of the wheel segments 40 on one side of the digester assembly 12 and advance radially from the inner edge 42 along the concave surface 48 as the biogas creates an upward rising force on each of the segments 40 to pass through the perforations 53 of each arcuate body 44 at the attachment point between each wheel segment 40 and the cylindrical body 18 as each of the wheel segments reach the top of the digester assembly 12 to form a an accumulated biogas pocket 58 at the top of the digester assembly 12.

The digester assembly also includes a waste input conduit 60. In one embodiment the waste input conduit 60 is a flexible hose, or alternatively, is any suitable conduit made of any suitable material for supplying agricultural waste 62 to a digester assembly 12. The waste input conduit 60 includes an open waste input end 64 for receiving agricultural waste 62 and a connecting end 66 connecting the waste input conduit 60 to the second end 32 of the hub 28 extending from the first cover 24 for delivering agricultural waste 62 through the first hub 28 and into the interior 20 of the digester assembly's 12 hollow cylindrical body 18.

The digester assembly also includes a waste output conduit 68, which, in one embodiment is a flexible hose, or alternatively, is any suitable conduit to facilitate the transport and expulsion of agricultural waste 62 out of the interior 20 of the digester assembly's 12 hollow cylindrical body 18. The waste output conduit 60 has an open waste output end 70 and a connecting end 72 connecting the waste output conduit 68 to the second end 38 of the hub 34 extending from the second cover 26 for delivering agricultural waste 62 through the second hub 34 and out of the interior 20 of the digester assembly's 12 hollow cylindrical body 18. In a preferred embodiment, the waste input 64 of the waste input conduit 60 is positioned higher than the waste output 70 of the waste output conduit 68 to facilitate the expulsion of agricultural waste 62 out of the interior 20 of the digester assembly's 12 hollow cylindrical body 18 via the pressure of biogas 58 accumulated within the interior 20 of the cylindrical body 18.

A biogas conduit 74 is also included in the digester assembly 12. In one embodiment, the biogas conduit 74 is a series of plastic pipes or tubing made of any suitable material, such as PVC or the like, or alternatively, is any known structure capable of transporting biogas. The biogas conduit 74 extends into the input end 64 and through the waste input conduit 60 and first hub 28 to extend upward within the conduit chamber 56 formed within the cylindrical body's 18 hollow interior 20. The biogas conduit includes a gas conduit inlet 76 within the conduit chamber, wherein the gas conduit inlet maintains a fixed position at the top of the digester assembly's 12 hollow cylindrical body 18 to encounter the biogas pocket 58 that is generated as the digester assembly 12 rotates, thereby permitting the produced biogas to flow into the biogas conduit 74 and out of the interior 20 of the cylindrical body 18 and digester assembly 12 to a power generation device 16. In a preferred embodiment, the gas conduit inlet 76 includes a valve assembly 78. In one embodiment, the valve assembly 78 is a float valve, or alternatively, is any is any known valve assembly capable of interacting with agricultural waste 62 such that when the volume of waste 62 level reaches a predefined level, the valve assembly 78 plugs the inlet 76 thereby preventing the produced biogas from flowing out of the interior 20 of the cylindrical body 18 while preventing waste 62 from entering the gas conduit 74.

A biogas bushing assembly 80 is also included within the interior of hub 28 of first cover 24. The biogas bushing assembly 80 supports biogas conduit 74 to maintain the gas conduit inlet's 76 fixed position within biogas pocket 58 at the top of the digester assembly 12. The biogas bushing assembly 80 includes a biogas conduit bushing 82, which in one embodiment, is a ring which rotatably surrounds biogas conduit 74 and a bushing leg 84 which is comprised of a narrow segment which fixedly attaches the conduit bushing 82 to the interior of hub 28 such that bushing assembly 80 rotates in unison with hollow cylindrical body 18 of digester assembly 12. While bushing leg 84 and conduit bushing 82 rotate around the fixed biogas conduit 74 as the hollow cylindrical body 18 rotates, the bushing assembly 80 supports the stationary biogas conduit 74 in a fixed position within hub 28 and hollow cylindrical body 18 to maintain the gas conduit inlet's 76 position at the top of the digester assembly 12 in communication with the biogas pocket 58. In an alternative embodiment, the digester assembly's 12 orientation and incoming waste 62 flow can be reversed and will operate using either end 64, 70 of either waste conduit 60, 68 as a waste inlet or outlet. Specifically, in such an embodiment, the position of the digester is reversed and either end 64, 70 can be used as an inlet by ensuring that whatever end 64, 70 of the digester assembly is desired as the outlet end is maintained in a lower position than the input end 70, 64, and inserting the biogas bushing assembly 80 and biogas conduit 74 into whatever conduit 60/68 and associated hub 28/34 is selected as the waste input.

The agricultural waste digester and biogas production system 10 also includes a water vessel 14. The water vessel 14 is filled with heated water 88, and is of an appropriate size and depth to receive the digester assembly 12 and allow the digester's 12 hollow cylindrical body 18 to freely spin when filled with agricultural waste 62 while partially submerged and floating within the water 88 of the water vessel 14. In one embodiment, the water vessel 14 is a water tank. Alternatively, the water vessel 14 is any known means by which water can be held, including but not limited to a tub, an above or in-ground concrete container, an earthen lake or lagoon, or the like.

In a preferred embodiment water vessel 14 includes a waste input conduit housing 90 extending outward from water vessel 14 in communication with the water 88 of the water vessel to house and support waste input conduit 60 extending upwardly at an angle out of water vessel 14. In one embodiment, waste input conduit housing 90 is a hollow rigid pipe, or alternatively, is any housing capable of supporting waste input conduit 60. Water vessel 14 also includes a waste output conduit housing 92 extending outward from water vessel 14 in communication with the water 88 of the water vessel to house and support waste output conduit 68 extending upwardly at an angle out of water vessel 14. In one embodiment, waste input conduit housing 90 is a hollow rigid pipe, or alternatively, is any housing 90 capable of supporting waste output conduit 68. Water vessel 14 also includes a pair of digester stabilizer assemblies 94 within interior of water vessel 14 to maintain the horizontal orientation of the hollow cylindrical body 18 and its center axis 22, ensuring that the hollow cylindrical body remains level as waste 62 is added. Each of digester stabilizer assembly 94 associated with first and second hubs 28 and 34 includes a digester hub bushing 96 which in one embodiment, is a ring which rotatably surrounds the hubs 28, 34 of the hollow cylindrical body 18.

Furthermore, each digester stabilizer assembly 94 includes a stabilizer leg 98 which fixedly attaches the hub bushings 96 to the interior of water vessel 14 to maintain the horizontal orientation of the hollow cylindrical body 18 and its center axis 22 as the body 18 rotates while floating partially submerged and filled with waste 62 in the warm water 88 of the water vessel 14. Specifically, although the water 88 supports the weight of the buoyant hollow cylindrical body 18, the hub bushings 96 and stabilizer legs 98 act to stabilize the body 18 to ensure that the hollow cylindrical body remains level as waste 62 is added.

The agricultural waste digester and biogas production system 10 also includes a power generation device 16. In one embodiment, the power generation device 16 is any apparatus capable of generating energy from biogas including but not limited to a motor, a heating device, or an electricity-generating engine. In addition, the power generation device 16 includes a heat exchanger 100 to utilize the heat generated by the operation of the power generation device 16 to heat the water 88 contained in the water vessel 14. Alternatively, the power generation device 16 is a biogas storage unit, capable of capturing and storing the produced biogas by the system, and the water vessel 14 is operably connected to a solar energy collection device 102 such that collected solar energy is used to heat the water 88 of the water vessel 14.

In operation, the digester assembly 12 is placed in the heated water 88 of the water vessel 14 and the water 88 is warmed to the proper temperature to produce optimum anaerobic digestion depending upon variables such as type and solid content of agricultural waste 62, digester 12 size, and the like. Agricultural waste 62, such as animal manure slurry, is fed into the input end 64 and flows through the waste input conduit 60 and first hub 28 into the interior 20 of the digester's 12 hollow cylindrical body 18, filling the digester assembly 12 with an appropriate amount of waste 62 slurry while ensuring that the digester is not filled completely full to capacity with waste 62. As the hollow cylindrical body 18 is filled with waste 62, the pair of digester stabilizer assemblies 94 rotatably support the first and second hubs 28, 34 of the hollow cylindrical body 18 to maintain the horizontal orientation of the hollow cylindrical body 18 and its center axis 22 as the body 18 is filled with waste 62 and begins to rotate while floating partially submerged and in the warm water 88 of the water vessel 14. Furthermore, waste 62 is permitted to be fed and flow into the digester assembly 12 without interference from the biogas conduit 74, as the biogas bushing assembly 80 maintains the biogas conduit 74 in a centered position relative to the waste input conduit 74 and first hub 78, allowing waste 62 to flow into the interior 20 of the cylindrical body 18 over the periphery of the conduit 74. Additionally, because the bushing leg 84 is comprised of a thin segment connecting the conduit bushing 82 to the interior of the hub 28, waste 62 is allowed to move past the leg 82 and into the interior 20 of the cylindrical body 18.

Once the digester 12 is supplied with the appropriate amount agricultural waste 62 slurry and any necessary additives, the buoyant digester 12 becomes partially submerged within the heated water 88 of the water vessel 14, and the heat from the water 88 is conducted to the digester assembly 12, warming the waste 62 slurry within the hollow cylindrical body 18 to initiate the digestion process. As the digestion process begins, the warmed waste 62 slurry begins to emit biogas within the digester's 12 hollow cylindrical body 18 to produce an ascending force upon the arcuate, contoured surface areas of the plurality of wheel segments 40 causing the cylindrical body 18 to rotate without additional energy added to the system. More specifically, due to the fixed attachment of each of the plurality of wheel segments 40 to the cylindrical body's 18 second cover 26 in addition to the contours of the internal structure of the cylindrical body 18 which permit the ascending force of biogas emitted from the waste 62 to be transferred to and trapped under the concave surfaces 48 of the wheel segments 40 positioned above adjacent wheel segments 40 on one side of the digester assembly while at the same time the biogas bubbles 55 positioned under the convex surfaces 50 of each wheel segment 40 are permitted to escape to the accumulated biogas pocket 58 at the top of the digester assembly 12, the wheel segments 40 form the spokes of a "reverse water wheel" which causes unidirectional rotation of the cylindrical body 18 about center axis 22, wherein biogas bubbles 55 accumulate into individual gas pockets 57 under the concave surfaces 48 of each of the wheel segments 40 on one side of the digester assembly 12 and advance radially upward from the inner edge 42 along the concave surface 48 as the biogas creates an upward rising force on each of the segments 40 and rotate the hollow cylindrical body 18. As each wheel segment reaches the top of the digester assembly 12, the individual biogas pocket 57 passes through the perforations 53 of each arcuate body 44 at the attachment point between each wheel segment 40 and the cylindrical body 18 to form a an accumulated biogas pocket 58 at the top of the digester assembly 12. In this manner, the digester assembly's 12 plurality of arcuate, contoured wheel segments 40 prevent biogas from moving freely out of the agricultural waste 62 and trap biogas under these segments 44 to utilize the force of the trapped biogas to rotate the cylindrical body 18 of the digester 12 and to create an induced agitation of the waste 62 from the rotation of the cylindrical body 18, which in turn, causes further biogas production in addition to waste 62 transport within the hollow cylindrical body 18 without necessitating the use of an agitator or a separate agitating device powered by an external power source. As the cylindrical body 18 rotates and each wheel segment 40 reaches the top of the body 18, the ascending biogas trapped by the concave surface 48 of the arcuate body 44 of the wheel segments 40 forms a biogas pocket 58 at the top of the digester assembly 12. Furthermore, because the plurality of contoured, arcuate wheel segments 40 having a curved surface area 48, 50 are fixedly attached to the hollow cylindrical body 18 to trap rising biogas within the interior 20 of the digester assembly 12, the wheel segments 40 form an inner structure within the digester assembly 12 which does not permit rising bubbles of air for agitation to freely flow throughout the waste 62. In addition, due to the arcuate bodies 44 of the plurality of wheel segments 40 having a curved surface area 48, 50 in addition to the cylindrical interior 20 of the hollow cylindrical body 18, the interior 20 of the digester assembly 12 contains no "dead corners" which allows for more complete mixing of waste 62 slurry content within the interior 20 of the digester assembly 12.

As the cylindrical body 18 rotates, the biogas bushing assembly 80 rotates in unison with the cylindrical body 18 while the biogas conduit bushing 82 rotatably surrounds and supports the stationary biogas conduit 74 in a fixed position such that the gas conduit's 74 inlet 76 is held within the conduit chamber 56 in a fixed position at the top of the digester assembly's 12 hollow cylindrical body 18 to encounter the biogas pocket 58 generated as the digester assembly 12 rotates, thereby permitting the produced biogas to flow into the biogas conduit 74 and out of the interior 20 of the cylindrical body 18 and digester assembly 12 to a power generation device 16.

As waste 62 continues to be supplied to the digester assembly 12, the waste level rises within the interior 20 of the hollow cylindrical body 18 and interacts with the valve assembly 78 connected to the inlet 76 of the biogas conduit 74, which in one embodiment is a float valve which rises with the rising level of the waste. Once the waste 62 reaches a predefined height within the interior 20 of the hollow cylindrical body 18, the valve assembly 78 plugs the inlet 76 thereby preventing the produced biogas from flowing out of the interior 20 of the cylindrical body 18 while preventing waste 62 from entering the gas conduit 74. With the flow of biogas into the biogas conduit 74 plugged by the valve assembly 78, the pressure of the biogas 58 within the interior 20 of the hollow cylindrical body 18 begins to rise. As the pressure rises and pressurized biogas is accumulated in the biogas pocket 58 at the top of the hollow cylindrical body 18, the rising pressure forces the waste 62 level down within the hollow cylindrical body 18, which in turn, creates an outward pressure upon the flexible waste input conduit 60 and the flexible waste output conduit 68 which causes waste 62 to be expelled out of the interior 20 of the hollow cylindrical body 18 into the flexible hose waste output and input conduits, 68, 60. However, because the input 64 of the waste input conduit 60 is oriented at a position higher than that of the waste output conduit's 68 waste output 72 in addition to the higher angle at which the waste input conduit 60 is maintained by the waste input housing 90, the increased pressure within the interior 20 results in the waste being forced out of the hollow cylindrical body 18 into the waste output conduit 68 and expelled out of the output end 70 of the waste output conduit 68. Once the digested waste 62 is expelled out of the digester assembly 12 via the waste output conduit 68, the waste level within the interior 20 of the hollow cylindrical body 20 drops causing the valve assembly to 78 to disengage from the inlet 76 of the biogas conduit 74 and allows the flow of biogas into the biogas conduit 74 to resume.

The biogas produced by the rotation and heat within the digester assembly 12 flows out of the digester assembly via the biogas conduit 74 to fuel and operate a power generation device 16. In embodiments wherein the power generation device 16 is an engine used to generate electricity, a heat exchanger 100 utilizes the energy given off by the operation of the engine power generation device 16 to heat the water 88 contained in the water vessel 14. Alternatively, a solar energy collection device 102 is provided which utilizes collected solar energy to heat the water 88 of the water tank 14.

In an alternative embodiment of the present invention, the agricultural waste digester and biogas production system 10 includes a waste transport conduit 104. In one embodiment the waste transport conduit 104 is a tube, or alternatively, is a hose or any suitable conduit to facilitate the transport and expulsion of agricultural waste 62 comprised of liquid waste materials, supernatant solid and/or partially dissolved solid waste materials, and sediment waste material 112 including viscous and/or non-buoyant solid and/or partially dissolved solid waste materials out of the interior 20 of the digester assembly's 12 hollow cylindrical body 18. The waste transport conduit 104 includes a first end 106 in communication with and extending from an opening or passage 108 disposed through the lateral cylindrical side wall 110 of the hollow cylindrical body 18 such that the waste transport conduit 104 is in communication with the agricultural waste 62 contained within the hollow interior 20 of the cylindrical body 18.

The waste transport conduit 104 also includes a conduit body 114 which extends outwardly from the exterior of the hollow cylindrical body 18 from the first end 106 attached in communication with the opening or passage 108 of the cylindrical body's sidewall 110 to a second end 116 in communication with an opening or passage 118 disposed through a side wall of a waste discharge conduit 120. The conduit body 114 is arcuate and has a curled or curvilinear contour which is oriented opposite of the direction of rotation 119 of the hollow cylindrical body 18. Preferably, the conduit body 114 extends axially outward from the side wall 110 of the hollow cylindrical body 18 to the waste discharge conduit 120 in a curvilinear fashion such that the conduit body 114 curves radially in a circumferential direction which is opposite of the orientation of the concave surfaces 48 of the wheel segments 40 within the hollow cylindrical body 18 and the direction of rotation 119 of the hollow cylindrical body 18.

Alternatively, the conduit body 114 of the waste transport conduit 104 is disposed within the interior 20 of the hollow cylindrical body 18 and the first end 106 includes an opening lying adjacent to an interior surface of the lateral cylindrical side wall 110 of the hollow cylindrical body 18 such that the waste transport conduit 104 is in communication with the agricultural waste 62. In the alternate embodiment disclosed immediately above, the second end 116 of the waste transport conduit 104 is disposed through an opening or passage 108 in the cylindrical body's sidewall 110 or in the second cover 26 and extends outwardly from the interior 20 of the hollow cylindrical body 18 attached in communication with the opening or passage 118 disposed through the side wall of the waste discharge conduit 120. The conduit body 114 is arcuate and as the conduit body 114 extends from its first end 108 to the conduit body's second end 116 connected to the waste discharge conduit 120, the body 114 has a curled or curvilinear contour which is oriented opposite of the direction of rotation 119 of the hollow cylindrical body 18 consistent with the former embodiment described above.

The waste discharge conduit 120, in one embodiment, is a rigid tube extending from an open waste output end 124 to a connecting end 122. The waste output conduit housing 92 which extends outward from water vessel 14 houses and supports the waste discharge conduit 120 and the open waste output end 124 extending upwardly at an angle out of water vessel 14, as well as further maintaining the orientation and stabilizing the end of the cylindrical body 18 opposite the first cover 24 during rotation. A rotatable and flexible joint 126, which, in one embodiment is a U-joint, connects the connecting end 122 of the waste discharge conduit 120 to the second cover 26 of hollow cylindrical body 18 such that the waste discharge conduit 120 rotates within the waste output conduit housing 92 in unison with the hollow cylindrical body 18 while maintaining its orientation within the waste output conduit housing 92.

The waste discharge conduit 120 further includes a waste movement device or auger 128. The auger 128 is disposed internally within the waste discharge conduit 120 and extends axially within the interior of the waste discharge conduit 120 from the open waste output end 124 to the connecting end 122. In a preferred embodiment, the auger 128 is fixed to the waste discharge conduit 120 such that as the hollow cylindrical body 18 rotates, the waste discharge conduit 120 and auger 128 housed therein rotate in unison with the hollow cylindrical body 18 such that the sediment waste material 112 as well as non-sediment liquid or supernatant waste 62 supplied to the interior of the waste discharge conduit 120 is conveyed to the waste output end 124 of the auger 128 and discharge conduit 120.

In operation, consistent with the initial disclosed embodiment of the present invention described above, the digester assembly 12 is placed in the heated water 88 of the water vessel 14 and agricultural waste 62 is fed into the interior 20 of the digester's 12 hollow cylindrical body 18. As the digestion process begins, the warmed waste 62 slurry begins to emit biogas within the digester's 12 hollow cylindrical body 18 to produce an ascending force upon the arcuate, contoured surface areas of the plurality of wheel segments 40 causing the cylindrical body 18 to rotate. During the digestion process and as the hollow cylindrical body 18 rotates, sediment waste material 112 including viscous waste materials and non-buoyant solid and/or partially dissolved solid materials within the agricultural waste 62 which has accumulated within the cylindrical body 18 falls into and enters the waste transport conduit 104 via the passage 108 through the cylindrical sidewall 110 (or alternatively through the open second end 116 of the conduit 104) as the passage 108 and the conduit's open end 116 rotate to a position along the bottom or lower surface of the hollow cylindrical body 18.

As the rotation of the hollow cylindrical body 18 continues, the conduit body's 114 arcuate shape and curled or curvilinear contour which is oriented opposite of the direction of rotation 119 of the hollow cylindrical body 18 prevents the sediment waste material 112 and additional agricultural waste 52 which is collected by and received within the waste transport conduit 104 from flowing into and reentering the interior 20 of the cylindrical body 18. Furthermore, the conduit body 114 extends from the hollow cylindrical body 18 to the waste discharge conduit 120 curving radially and outwardly in a circumferential direction which is opposite of the orientation of the concave surfaces 48 of the wheel segments 40 within the hollow cylindrical body 18 and the direction of rotation 119 of the hollow cylindrical body 18. This contour prevents the waste 52 and sediment 112 materials contained therein from emptying back into the cylindrical body 18 and creates a unidirectional, curvilinear flow path such that the waste 52 and sediment 112 materials are transmitted or "rolled" through the transport conduit 104 to the waste discharge conduit 120 as the conduit 104 rotates in unison with the cylindrical body 18.

Once the sediment waste material 112 is transmitted through the waste transport conduit 104 via the arcuate contour of the conduit acting in concert with the rotation of the cylindrical body 18, the sediment waste material 112 empties out of the second end 116 of the transport conduit 104 into the waste discharge conduit 120 through the opening or passage 118 therein. Furthermore, non-sediment liquid and supernatant agricultural waste 62 is additionally caused to flow through the transport conduit 104 by either or both of gas pressure or as a result of pressure equilibrium as more agricultural waste 62 is introduced into the digester 12.

The sediment waste material 112 as well as non-sediment liquid or supernatant waste 62 supplied to the interior of the waste discharge conduit 120 are engaged by the auger 128 which rotatably conveys the material therein to the waste output end 124 and out of the digester 12 via the fixed connection between the auger 128 and the discharge conduit 120 which rotate in unison with the hollow cylindrical body 18.

In this manner, a scalable, inexpensive, and effective agricultural waste digester and biogas production system 10 is presented that is designed with a contoured, fixed internal structure with wheel segments 40 which trap produced biogas to prevent the gas from moving freely out of the waste 62 thereby utilizing the ascending force of the trapped biogas to both rotate the digester 12 and induce the agitation of the agricultural waste 62 as the digester's 12 entire cylindrical body 18 rotates without the use of an agitator to provide more complete mixing of waste content 62 without additional energy added to the system. Furthermore, the arcuate transport conduit 104 as disclosed by the additional embodiment of the present invention effectively removes dense sediment waste materials 112 within the hollow cylindrical body 12 and prevents the buildup of sediment. The removal of such buildup lessens the structural material needed, reduces costs and allows the cylindrical body to float, in addition to overcoming problems presented by sediment buildup requiring pre-digestion separation and/or complete cleanout, diminished efficiency, and ultimately system failure. As a result at the very least all of the stated objectives have been met.

It will be appreciated by those skilled in the art that other various modifications could be made to the device without the parting from the spirit and scope of this invention. All such modifications and changes fall within the scope of the claims and are intended to be covered thereby.

What is claimed is:

1. A rotatable agricultural waste digester and biogas generation system comprising:
   a water vessel containing water;
   a buoyant digester assembly disposed within the water vessel having a cylindrical body, a hollow interior, a center axis, a waste input conduit, a waste discharge conduit, and a plurality of wheel segments within the interior of the digester assembly;
   a gas conduit extending from the interior of the digester assembly to a power generation device through the waste input conduit; and
   wherein the plurality of wheel segments include uniformly oriented concave surfaces and are each fixedly attached to the cylindrical body and extend toward the center axis such that ascending biogas within the digester assembly is trapped under the concave surfaces on one side of the digester assembly such that the cylindrical body rotates about the center axis.

2. The rotatable agricultural waste digester and biogas generation system of claim 1 wherein each of the plurality of wheel segments are fixedly attached to the cylindrical body at an outer edge and include a plurality of perforations at the outer edge.

3. The rotatable agricultural waste digester and biogas generation system of claim 1 wherein the plurality of wheel segments include uniformly oriented convex surfaces on a side of the arcuate bodies opposite the concave surfaces.

4. The rotatable agricultural waste digester and biogas generation system of claim 1 wherein the cylindrical body is closed at both ends by a first and second cover.

5. The rotatable agricultural waste digester and biogas generation system of claim 1 wherein the gas conduit includes a valve assembly actuated by agricultural waste within the digester.

6. The rotatable agricultural waste digester and biomass biogas generation system of claim 5 wherein the valve assembly is a float valve.

7. The rotatable agricultural waste digester and biomass biogas generation system of claim 5 wherein the valve assembly is configured to plug an inlet of the gas conduit when waste reaches a predefined level.

8. The rotatable agricultural waste digester and biogas generation system of claim 1 wherein the cylindrical body is enclosed at both ends by a first cover having a first hub and a second cover having a second hub.

9. The rotatable agricultural waste digester and biogas generation system of claim 1 wherein the gas conduit has a gas conduit inlet having a fixed position at a top of the cylindrical body.

10. The rotatable agricultural waste digester and biogas generation system of claim 9 wherein the gas conduit within the cylindrical body is fixedly positioned such that the gas conduit inlet of the gas conduit encounters a biogas pocket within the cylindrical body.

11. The rotatable agricultural waste digester and biogas generation system of claim 1 wherein the hollow interior of the cylindrical body has a wall that separates the wheel segments from a conduit chamber.

12. The rotatable agricultural waste digester and biogas generation system of claim 1 further comprising a waste transport conduit in communication with agricultural waste within the interior of the cylindrical body, wherein the waste transport conduit extends from the cylindrical body to the waste discharge conduit.

13. The rotatable agricultural waste digester and biogas generation system of claim 12 wherein the waste transport conduit includes a conduit body which extends outwardly from the cylindrical body from a first end attached to a side wall of the cylindrical body to a second end attached to the waste discharge conduit.

14. The rotatable agricultural waste digester and biogas generation system of claim 13 wherein the body of the waste transport conduit has a curved contour as the body extends from the cylindrical body to the waste discharge conduit.

15. The rotatable agricultural waste digester and biogas generation system of claim 12 additionally comprising an auger disposed within the waste discharge conduit.

16. The rotatable agricultural waste digester and biogas generation system of claim 15 wherein the second end of the waste discharge conduit is connected to the cylindrical body via a rotatable joint such that the waste discharge conduit rotates in unison with the cylindrical body and the waste transport conduit.

17. The rotatable agricultural waste digester and biogas generation system of claim 16 wherein the auger is fixedly attached to the interior of the waste discharge conduit such that the auger rotates in unison with the waste discharge conduit and the cylindrical body.

18. A method of generating biogas from agricultural waste comprising the steps of providing a rotating buoyant digester and biogas generation system according to claim 1, wherein the water vessel contains heated water; supplying the interior of the digester with agricultural waste to generate biogas; placing the digester into the heated water of the water vessel; and providing a waste transport conduit in communication with agricultural waste within the interior of the cylindrical body wherein the waste transport conduit extends from the cylindrical body to the waste discharge conduit.

19. The method of generating biogas from agricultural waste of claim 18 further comprising the step of transporting agricultural waste and sediment from the cylindrical body to the waste discharge conduit through the waste transport conduit as the cylindrical body rotates.

20. The method of generating biogas from agricultural waste of claim 19 wherein the agricultural waste and sediment is transported through the waste transport conduit in a direction opposite to a direction of rotation of the cylindrical body.

21. The method of generating biogas from agricultural waste of claim 20 further comprising the step of conveying the agricultural waste and sediment out of the digester assembly through the waste discharge conduit.

22. The method of generating biogas from agricultural waste of claim 21 wherein the agricultural waste and sediment is conveyed out of the digester assembly through the waste discharge conduit by an auger disposed within the waste discharge conduit.

\* \* \* \* \*